(12) United States Patent
Paschetto et al.

(10) Patent No.: US 8,865,474 B2
(45) Date of Patent: Oct. 21, 2014

(54) AUTOMATED LABORATORY SYSTEM

(75) Inventors: Michael Paschetto, Hampden, MA (US); Peter Massaro, Burlington, CT (US); Jeff Boot, Sudbury, MA (US); David Wilson, Winchester, MA (US)

(73) Assignee: Protedyne Corporation, Windsor, CT (US)

( * ) Notice: Subject to any disclaimer, the term of this patent is extended or adjusted under 35 U.S.C. 154(b) by 1287 days.

(21) Appl. No.: 11/429,888

(22) Filed: May 8, 2006

(65) Prior Publication Data

US 2006/0201810 A1 Sep. 14, 2006

Related U.S. Application Data

(63) Continuation of application No. 10/026,918, filed on Dec. 18, 2001, now abandoned.

(60) Provisional application No. 60/256,173, filed on Dec. 18, 2000.

(51) Int. Cl.
| | |
|---|---|
| *G01N 33/559* | (2006.01) |
| *G01N 35/00* | (2006.01) |
| *G01N 27/447* | (2006.01) |
| *B01L 3/02* | (2006.01) |
| *G01N 35/04* | (2006.01) |

(52) U.S. Cl.
CPC ...... *G01N 35/0099* (2013.01); *G01N 27/44704* (2013.01); *G01N 27/44747* (2013.01); *B01L 3/0244* (2013.01); *B01L 3/0275* (2013.01); *G01N 27/44782* (2013.01); *G01N 35/04* (2013.01)
USPC ........... 436/177; 422/504; 204/466; 204/471; 204/470; 204/616; 204/619; 204/620

(58) Field of Classification Search
CPC .................. G01N 27/44704; G01N 27/44747; C25D 13/00; C25D 17/00
USPC .......................................... 436/177; 422/504
See application file for complete search history.

(56) References Cited

U.S. PATENT DOCUMENTS

| | | | |
|---|---|---|---|
| RE28,437 | E | 6/1975 | Devol et al. |
| 3,923,463 | A | 12/1975 | Bagshawe et al. |

(Continued)

FOREIGN PATENT DOCUMENTS

| | | | |
|---|---|---|---|
| DE | 19853184 | A1 | 6/2000 |
| EP | 0293010 | A | 11/1988 |

(Continued)

OTHER PUBLICATIONS

European Search Report 01991224.5 dated Nov. 6, 2006.

*Primary Examiner* — Lyle Alexander
(74) *Attorney, Agent, or Firm* — Wolf, Greenfield & Sacks, P.C.

(57) ABSTRACT

An automated laboratory system and method allow high-throughput and fully automated processing of materials, such as liquids including genetic materials. The invention includes a variety of aspects that may be combined into a single system. For example, processing may be performed by a plurality of robotic-equipped modular stations, where each modular station has its own unique environment in which processes are performed. Transport devices, such as conveyor belts, may move objects between modular stations, saving movement for robots in the modular stations. Gels used for gel electrophoresis may be extruded, thus decreasing the time needed to form such gels. Robotically-operated well forming tools allow wells to be formed in gels in a registered and accurate way.

13 Claims, 8 Drawing Sheets

(56) References Cited

U.S. PATENT DOCUMENTS

| | | |
|---|---|---|
| 4,298,308 A | 11/1981 | Richter |
| 4,379,335 A | 4/1983 | Kirsch et al. |
| 4,507,044 A | 3/1985 | Hutchins et al. |
| 4,510,684 A | 4/1985 | Hutchins et al. |
| 4,578,764 A | 3/1986 | Hutchins et al. |
| 4,586,151 A | 4/1986 | Buote |
| 4,616,514 A | 10/1986 | Magnussen, Jr. et al. |
| RE32,414 E | 5/1987 | Hutchins et al. |
| 4,692,308 A | 9/1987 | Riley et al. |
| 4,708,886 A | 11/1987 | Nelson |
| 4,727,494 A | 2/1988 | Buote |
| 4,790,183 A | 12/1988 | Pfost et al. |
| 4,795,612 A | 1/1989 | Keller |
| 4,835,711 A | 5/1989 | Hutchins et al. |
| 4,846,003 A | 7/1989 | Marquiss |
| 5,046,539 A | 9/1991 | MacLeish et al. |
| 5,056,028 A | 10/1991 | Ohta et al. |
| 5,063,790 A | 11/1991 | Freeman et al. |
| 5,087,423 A | 2/1992 | Ishibashi |
| 5,104,621 A | 4/1992 | Pfost et al. |
| 5,147,610 A | 9/1992 | Watanabe et al. |
| 5,149,654 A | 9/1992 | Gross et al. |
| 5,150,288 A | 9/1992 | Imai et al. |
| 5,207,986 A | 5/1993 | Kadota et al. |
| 5,255,197 A | 10/1993 | Iida |
| 5,463,564 A | 10/1995 | Agrafiotis et al. |
| 5,497,670 A | 3/1996 | Carl |
| 5,518,686 A | 5/1996 | Masterson et al. |
| 5,544,535 A | 8/1996 | Thomas |
| 5,578,269 A | 11/1996 | Yaremko et al. |
| 5,602,756 A | 2/1997 | Atwood et al. |
| 5,660,792 A | 8/1997 | Koike |
| 5,770,860 A | 6/1998 | Franen |
| 5,827,745 A | 10/1998 | Astle |
| 5,846,395 A | 12/1998 | Sarrine et al. |
| 6,037,186 A | 3/2000 | Stimpson |
| 6,068,393 A | 5/2000 | Hutchins et al. |
| 2002/0176801 A1 | 11/2002 | Giebeler et al. |

FOREIGN PATENT DOCUMENTS

| | | | |
|---|---|---|---|
| EP | 63313056 | * | 12/1988 |
| EP | 1045036 | A2 | 10/2000 |
| EP | 0998979 | A | 5/2005 |
| FR | 2726652 | A | 5/1996 |
| JP | 63313056 | A | 12/1988 |

* cited by examiner

AUTOMATED LABORATORY SYSTEM

RELATED APPLICATIONS

This application is a continuation of U.S. application Ser. No. 10/026,918, filed Dec. 18, 2001, and which claims benefit under 35 U.S.C. §19(e) to U.S. Provisional Application 60/256,173, filed Dec. 18, 2000, which are hereby incorporated by reference in their entirety.

FIELD OF THE INVENTION

This invention relates to automated laboratory processing, such as automated genomic research.

BACKGROUND OF THE INVENTION

Various laboratory processes, such as those performed in genomic research, are largely performed by hand and/or with substantial human intervention at points in the process. Thus, performing such research can be time-consuming, labor-intensive and relatively low volume. Moreover, the required human intervention in semi-automated processes or manually-performed operations increases the likelihood that materials used in the process will become contaminated or that processes are not repeatable, e.g., will be performed in different ways during different tests.

SUMMARY OF THE INVENTION

The inventors have developed a variety of unique tools, processes and devices that make high-throughput and fully-automated laboratory processes, such as those performed for genomic research, possible. Thus, the invention includes various aspects that may be used independently or in a variety of sub-combinations, and aspects may be combined into a single system or method for performing automated laboratory processes.

In one illustrative embodiment, a plurality of modular stations may be combined into a single material processing system. Each modular station may perform at least one automated process in an overall process sequence. Each modular station may have its own controlled environment unique to the modular station within which to perform its processes, and may be capable of providing material for further processing by another module station without human handling of the material. That is, although two or more modular stations may be nominally controlled to have similar environmental conditions, e.g., the same temperature or humidity, the modular stations have their own unique environment since the environments of the modular stations are not well connected. Thus, processes may be performed at each modular station in a controlled environment that prevents cross-contamination between modular stations or contamination by outside sources. Further, since human handling of materials is not necessarily required to perform processes at a modular station, and processed material may be provided to another modular station for further processing without human intervention, the likelihood of contamination by human or other sources is decreased and the processing steps are more highly repeatable.

In one illustrative embodiment, a method for processing genetic material, such as DNA, includes inputting a genetic material into an automated processing system, and performing at least amplification and separation processes using the genetic material without requiring human handling of the genetic material. Thus, in accordance with this illustrative embodiment, genetic material may be at least amplified, such as by a PCR process, and separated, such as by gel electrophoresis, without requiring any human handling of the genetic material. This is in contrast to amplification and separation processes typically performed in laboratories, in which a human is required to place and remove genetic material at a PCR processing station, and again handle the amplified genetic material so that it can be separated, e.g., by manually pipetting genetic material into wells formed in an agarose gel and submitting the gel to a voltage separation process. Such human handling at various steps in the processing may contaminate the genetic material and/or result in improper or imperfect processes being performed.

In another illustrative embodiment, modular stations may operate to perform parallel processing of material samples. This is in contrast to other types of systems in which material samples or sample holders are processed serially. For example, the modular stations operating in accordance with one aspect of the invention may control a robot to remove several sample holders from a storage area and place the sample holders in a work tray. The robot may then perform the same or similar liquid handling procedures on the materials in the sample holders. Once the liquid handling processes are completed for all of the sample holders, the robot may move the sample holders to an area where they are transported to another modular station for further processing. This is only one example of a type of parallel processing that can save time and increase throughput since the robot can be tasked to perform several similar processes using a same tool, and then change tools to perform another set of processes. Using the example above, the robot may use a gripping tool to move sample holders to the work tray, then exchange the gripping tool for a liquid handling tool to perform liquid handling processes on the sample holders in the work tray. Only one tool exchange is needed to process multiple sample holders. In a serial process, the robot would position one sample holder in a work area, exchange tools, perform liquid handling processes on the sample holder, exchange tools again, move the sample holder from the work area so it can be transported to another modular station and retrieve another sample holder for processing. Other savings in addition to reduced tool exchanges may be realized using parallel processing. For example, all of the sample holders in a work tray may be scheduled to receive a same reagent mixed with the samples held in the holders, but in different amounts. Thus, the robot using the liquid handling tool may pick up a relatively large amount of the reagent from a reagent source (such as a reagent filled cup) and then deposit different amounts in the holders without returning to the source. This processing can avoid wasted movement of the robot between a reagent source and the holders. Parallel processing can be very effective in improving throughput when samples or sample holders to receive the same or similar processing are grouped together. Thus, in another illustrative embodiment, samples or sample holders that are planned to receive the same or similar processing may be grouped together for parallel processing, e.g., by a control system analyzing the process plans for each of the samples or sample holders and logically grouping the samples or sample holders together.

In another illustrative embodiment, modular stations and the processes performed by them are controlled by a database-driven control system. Serial processing such as that described above allows for a simple control system since multiple ongoing processes and positions of sample holders need not be tracked simultaneously, or nearly simultaneously. The control system in this embodiment provides a much more flexible system, since the control system can support serial or parallel processing at the modular station level and/or at the process step level within each modular station. For example, the control system may use a relational database to track and implement processes within a system. Sample holders may each have their own unique identification, e.g., a bar code character string, that is associated one or more database tables that define the processing to be performed on the material in the sample holders. This type of control system arrangement can provide for a powerful and flexible system since a plurality of processing tables may be predefined and associated with samples or sample holders in different ways to provide different processing plans. For example, tables in the database may be constructed to describe/control Processes 1 through 4. A first sample holder may be associated with and processed according to the tables for Processes 2, 4 and 3, in that order. A second sample holder may be associated with and processed according to the tables for Processes 2, 3 and 4, in that order. Thus, no structural change may be needed for the control system to provide different processing schemes for different samples, and there is no need to construct lengthy processing plans for each individual sample holder or sample. Instead, using the example above, predefined processing tables may be rearranged and associated with different sample holders to provide a plurality of different processing schemes. This type of relational-database driven control system can also allow more rapid analysis of planned processes when determining how to group sample holders for parallel processing. For example, a relatively simple determination may be made regarding which sample holders are associated with the table for Process 2. Those sample holder associated with Process 2 may be grouped together and processed in parallel, at least for that step in the process.

In another illustrative embodiment, an automated material processing system having a plurality of modular stations may use a non-robotic transport system to move material between the modular stations. For example, one or more conveyor belts may interconnect modular stations to perform material transport. The conveyors may be bi-directional so that material can be moved in either direction between modular stations. By using the non-robotic transport system, robots in each of the modular stations may move a more limited amount when transferring material from one modular station to another. That is, a robot need not be required to physically move a material to a location that is accessible by another robot in a next modular station so that the other robot can pick up the material and move it for further processing. Instead, the robot need only be required to place the material on a conveyor belt, for example, within the robot's own modular station. The conveyor can then move the material to a next modular station where a robot associated with the next modular station can access the material. This savings in robot movement can speed processes within a modular station (because of the more limited movement requirements of the robot), as well as greater physical separation between modular stations. Greater physical separation between modular stations may be useful for allowing easier human access, e.g., for repair, monitoring or other activities, and/or allow better isolation between environments within each modular station.

In another illustrative embodiment, a modular station may include a robot controlled liquid handler, or pipetting, tool that is used to move liquid material Within the modular station. The liquid handler may be a multi-channel device having a plurality of plungers, one plunger associated with each channel, to control the amount of fluid material that is drawn into and expelled from each pipette tip. Such plunger arrangements are well known in the art, but in this illustrative embodiment, plunger movement is controlled by a linear servo motor and linear encoder. The linear servo motor and/or linear encoder provide a much more rapid and accurate operation of the liquid handler than rotary stepper motor-driven pipetting systems known in the art, because the linear servo motor, with position and/or velocity feedback from the linear encoder, can move the plungers much faster and more accurately than a stepper motor system. The liquid handler tool may change the pipette tips used for each of the channels as is known in the art. However, in one illustrative embodiment, the liquid handler can confirm that the pipette tips have been removed and/or are properly positioned on the liquid handler using one or more sensors. For example, the liquid handler may move the attached pipette tips near a photosensor that detects the presence or absence of pipette tips at each of the channels. If a pipette tip is missing or misaligned, the liquid handler can eject one or more of the tips and replace the missing or misaligned tips as needed.

In another illustrative embodiment, gel material, such as that used to separate genetic material in an electrophoresis process, is formed by extrusion. This is in contrast to typical gel-forming methods, in which warm liquid material is poured into a tray and allowed to set in a gel form within the tray. Using the extrusion process in this embodiment, liquid gel material may be supplied into an extrusion cavity between two cooled plates. As the liquid material moves along the cavity between the plates, the liquid is cooled and forms a gel that is extruded from the cavity. This process allows gels to be formed at a much more rapid pace as compared to conventional methods.

In one illustrative embodiment, a gel extruder includes a reservoir that holds relatively warm liquid material, such as an agarose mixture. This liquid material is supplied by a pump under pressure to an input side of an extruder cavity. The extruder cavity is formed by substantially parallel metal plates that are cooled, e.g., by a circulating chilled liquid such as water. Pressure of the incoming liquid material into the extruder cavity forces the liquid material along the extruder cavity and between the plates. The plates on either side of the cavity cool the liquid so that a semi-solid gel is formed and forced out of the extruder cavity. The gel extruder may also include a cutting device to cut the extruded gel into desired sizes and/or shapes, as well as a gel loading mechanism that places cut gels into trays or other carriers. The extrusion, cutting and tray loading process may be fully automated and not require any human handling or operation in the process.

In another illustrative embodiment, constituent portions of a material, such as genetic fragments in a liquid, may be separated using an automated process. For example, a robot-controlled tool may form wells in gel material and subsequently fill the wells with a liquid material to be separated, e.g., by gel electrophoresis. The robot may use a comb-like element that is inserted into the gel by the robot to form the wells. The comb-like element may be heated, for example, by electro-resistance heating, so that heated tines of the comb-like element form the wells in the gel. The robot may then exchange the comb-like well forming element for a liquid handling device, such as a pipetting device described above. Since the robot was used to form the wells in the gel, the robot can easily register the well positions formed in the gel with pipette tips in the liquid handling tool. Other portions of the separation process may also be automated, such as by having a robot move a gel that has wells filled with material to be separated to an electrophoresis voltage station, where the gel is subjected to an electric field to separate the material. The electrophoretically-separated material may be automatically picked, e.g., by a coring process, using a robotic picking tool.

The robot may use a vision system to identify and select separated material in the gel for picking. The picked, separated material may be used in further processing, such as further analysis, testing and so on.

These and other aspects of the invention will be apparent from the detailed description and claims below.

BRIEF DESCRIPTION OF THE DRAWINGS

Illustrative embodiments incorporating various aspects of the invention are described with reference to the following drawings, in which like reference numerals reference like elements, and wherein.

DETAILED DESCRIPTION

Illustrative embodiments that incorporate various aspects of the invention are described below in connection with the figures. However, it should be understood that the invention is not limited to the illustrative embodiments described below.

Figure 1:
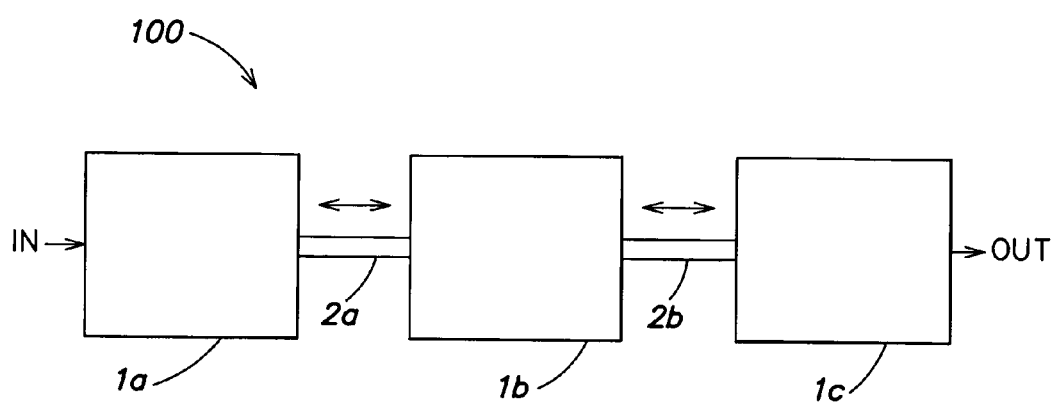
FIG. 1 is a schematic block diagram of a material processing having a plurality of modular stations in an illustrative embodiment.

FIG. 1 is a schematic diagram of a material processing system 100 in an illustrative embodiment in accordance with the invention. In this illustrative embodiment, the material processing system 100 includes three modular stations 1 that are interconnected by transport devices 2. Although in this illustrative embodiment, the material processing system 100 includes three modular stations 1, systems may include any suitable number of modular stations. Further, modular stations 1 may be interconnected by two or more transport devices 2. Moreover, although the material processing system 100 is shown as being a linear arrangement of modular stations, parallel arrangements of modular stations 1 or other suitable arrangements may be used. For example, in this illustrative embodiment, a single modular station 1B communicates with the modular stations 1A and 1C. However, the modular station 1B may be replaced with two or more modular stations 1 that communicate with the modular stations 1A and 1C. Such parallel processing arrangements may be used to improve the throughput of the system 100, e.g., where the processes performed by the modular station 1B take significantly longer than processes performed by the modular stations 1A and 1C.

In this embodiment, the material processing system 100 performs liquid material handling processes as well as genetic material amplification and separation processes. Thus, although a material processing system 100 in accordance with the invention may be arranged to perform any other suitable process or set of processes, in this illustrative embodiment, the material processing system 100, its modular stations 1, and other portions are described in connection with performing a genetic material handling, amplification and separation process. The material processing system 100 in this embodiment includes a liquid handling modular station 1A, an amplification modular station 1B, and a separation modular station 1C. As their names suggest, the liquid handling modular station 1A receives input genetic material, e.g., DNA fragments in a liquid solution, and performs the various liquid handling procedures needed to perform at least the amplification portions of the process. That is, the liquid handling modular station 1A can divide the input liquid material samples into multiple samples that are subjected to further processing. A more detailed description of the liquid handling processes performed in the modular station 1A is provided below.

The amplification modular station 1B receives liquid material samples, e.g., in a plurality of microtiter plates or other sample holders, from the modular station 1A by the transport device 2A and subjects the liquid material in the microtiter plates to amplification processes, such as those performed in typical polymerase chain reaction (PCR) processes. Thus, a robot within the amplification modular station 1B may place the microtiter plates in a PCR thermocycling device, which performs at least some, if not all, of the temperature cycling steps needed to perform PCR amplification of the genetic material.

Liquid material processed by the amplification modular station 1B may be sent back by the transport device 2A to the liquid handling modular station 1A, if necessary for further liquid handling processes, or may be transferred by the transport device 2B to the separation modular station 1C. The separation modular station 1C may use the received liquid material, e.g., again in microtiter plates, to separate the various constituents in the liquid material samples in each well of the microtiter plates. Any suitable separation process may be performed, such as capillary electrophoresis, gel electrophoresis, and so on. In this illustrative embodiment, the materials are separated using a gel electrophoresis process. Thus, a robot in the separation modular station 1C may use a liquid handling device to place liquid material in the microtiter plate wells into wells formed in a gel material. The gels may be automatically produced using a gel extrusion process described in more detail below. Moreover, the robot may use a well-forming tool to automatically form wells in the gels. The robot may then subject the gels to an electric field at a voltage station and pick selected portions of the separated material once the electrophoresis process is complete.

The fully-automated nature of the material processing system 100 means that a human operator may input liquid material into the liquid handling modular station 1A and not again handle the liquid material or any other tools or other materials used in the process. Instead, for example, the human operator may receive separated genetic material from the gels at the separation modular station 1C.

Figure 2:
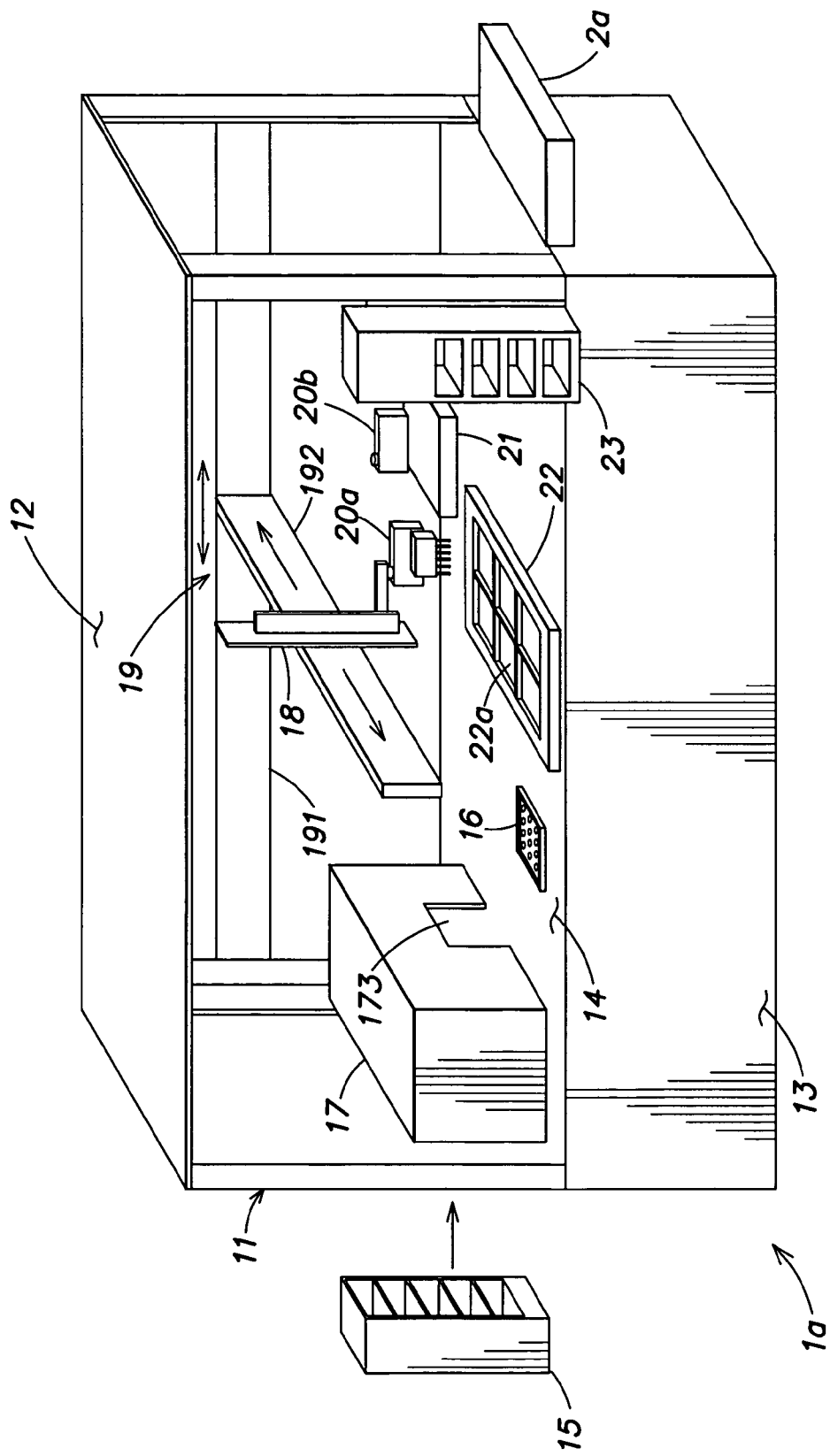
FIG. 2 is a schematic diagram of a liquid handling modular station in an illustrative embodiment.

FIG. 2 shows an illustrative embodiment of a liquid handling modular station 1A. In this illustrative embodiment, the modular station 1A has a frame 11 in the form of a box-like structure including uprights at four corners and is covered by a top surface 12. Skirt panels 13 enclose a lower portion of the frame 11 on four sides of the modular station 1A. These skirt panels 13 may have doors, access panels, or any other suitable features to allow access to equipment located under a work surface 14 that extends between the frame uprights at the top edges of the skirt panels 13. A variety of different types of equipment may be located in the space covered by the skirt panels 13 and the work surface 14, such as air filters, heat exchangers, air conditioning devices, liquid storage tanks, electric service panels, computer hardware, and so on. Although in FIG. 2 the upper portion of the modular station 1A above the work surface 14 is shown as being open, this work space between the work surface 14 and the top surface 12 is preferably enclosed by panels extending between the frame 11 uprights. The enclosing panels may be made of a transparent or semitransparent material, such as glass or an acrylic material, and may also have doors to allow access to the work space. These enclosing panels may allow the environment in which processes are performed by the modular station 1A to be controlled. For example, the humidity, temperature and other environmental features inside the enclosed work space may be controlled, e.g., air or other gas mixtures in the work space may be filtered, such as by an HEPA filter or other filtering device, and so on.

In this illustrative embodiment, although the modular station 1A may be arranged to perform different functions, the modular station 1A in this embodiment performs liquid handling processes for genetic amplification and screening. Liquid material samples are provided in sample holder 16, such as commonly used microtiter plates, that are loaded into hotels 15. The hotels 15 may include a plurality of vertically-oriented shelves 152 (see FIG. 3) on which the sample holders 16 are placed. Hotels 15 may be loaded into a storage box 17, e.g., by opening a door on an enclosing panel of the modular station 1A and placing the hotel 15 into the storage box 17. Loading of hotels 15 into the storage box 17 may be done manually, or by machine.

Figure 3:
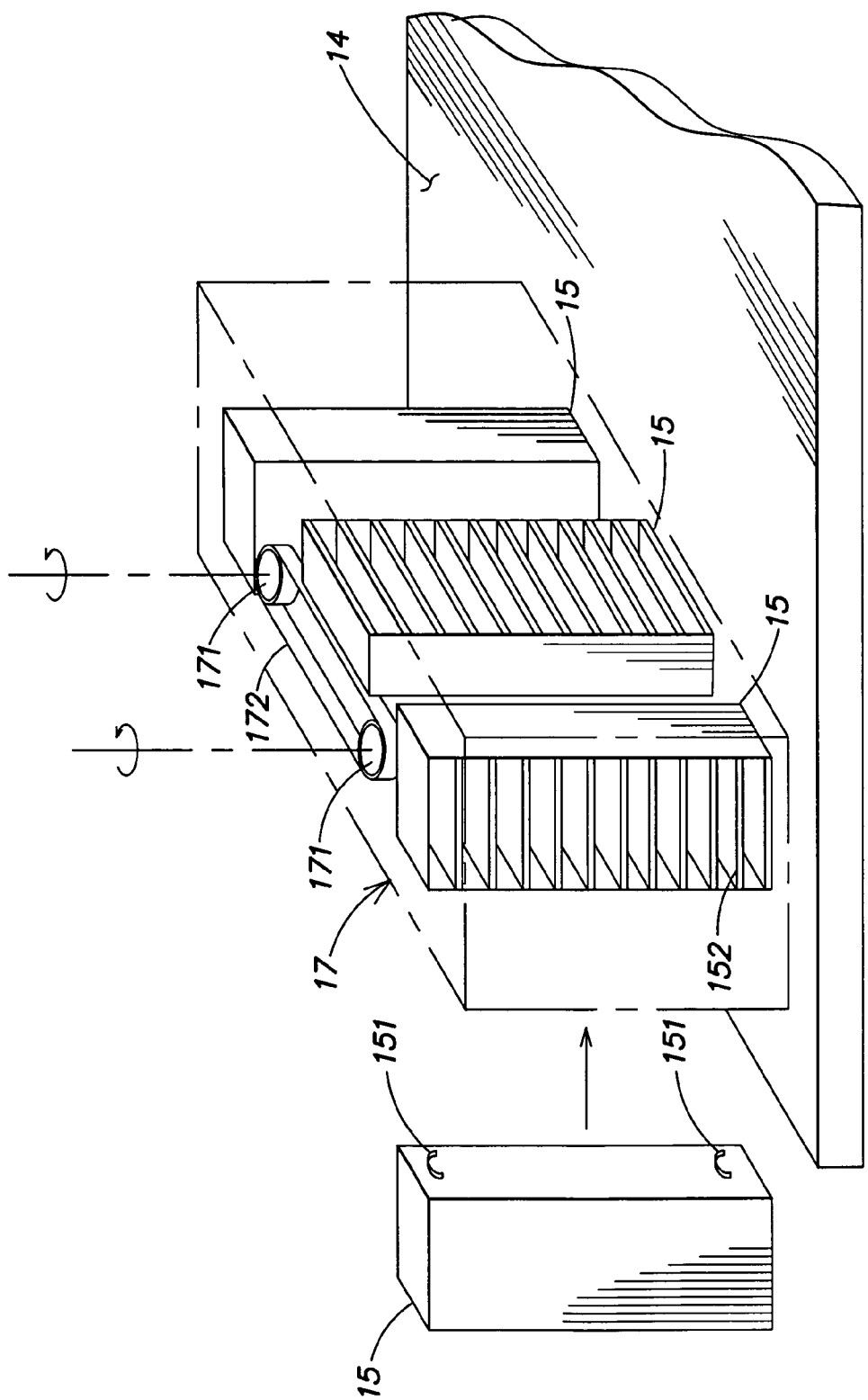
FIG. 3 is a schematic diagram of a sample holder storage box in an illustrative embodiment.

FIG. 3 shows a schematic diagram of a storage box 17 in an illustrative embodiment. The storage box 17 is enclosed on its six sides so that the environment in which the hotels 15 are stored can be controlled. That is, in one aspect of the invention, the environment within the storage box 17 may be different from the environment within the enclosed work space or other work areas in the modular station 1A. Sides of the storage box 17 may have access doors or other features to allow the hotels 15 to be placed inside the storage box 17 and/or to allow removal of sample holders 16 from the hotels 15. In this illustrative embodiment, the hotels 15 have hooks 151 that allow the hotels 15 to be hung on one or more belts 172. Although only one belt 172 is shown in FIG. 3, two or more belts 172 may extend around vertical shafts 171 in the storage box 17. The shafts 171 may rotate as shown in FIG. 3 so that the belts 172 are driven in a rotary direction. Driving the belts 172 in the rotary direction creates a carousel-type arrangement in which the hotels 15 can be moved in a rotary fashion in the storage box 17. The shafts 171 may be driven by a motor drive system (not shown) that is positioned below the work surface 14 and may be controlled so that particular hotels 15 and/or particular sample holders 16 are positioned at any desired position within the storage box 17. For example, each of the hotels 15 may have a bar code or other machine readable identification code so that each hotel 15 can be uniquely identified. For example, a bar code label on the hotel 15 may be read by a bar code reader as the hotels 15 are loaded into the storage box 17. Each of the sample holders 16 may similarly have a machine readable code so that each sample holder 16 can be uniquely identified. Again, the machine readable codes on the sample holders 16 may be read as an associated hotel 15 is loaded into the storage box 17 or while the hotels 15 are moved within the box 17. Knowing which sample holders 16 are supported on which shelf 152 in which hotel 15 may allow a control system to drive the belts 172 to position a hotel 15 at a desired position in the box 17, e.g., so that a particular sample holder 16 can be accessed.

It should be understood that as with all of the embodiments described herein, the illustrative embodiment shown in FIG. 3 depicts only one possible way in which samples holders 16 or other carriers of the liquid material may be handled. For example, hotels 15 may not be made removable from the storage box 17, and instead the sample holders 16 may be individually loaded onto the shelves 152 in the hotels 15 while the hotels 15 are in the storage box 17. Alternately, the hotels 15 may not be used at all, and instead the sample holders 16 may be stored in other ways. For example, the storage box 17 may include a plurality of vertically-oriented shelves that are open to access from both the outside of the modular station 1A (so that sample holder 16 may be placed on the shelves from the outside) and from inside the modular station 1A (so that a robot or other device can remove the sample holder 16 from the shelves).

In this illustrative embodiment, the modular station 1A includes a robot that performs many of the processing steps performed in the modular station 1A. The robot 18 in this embodiment is an inverted three-axis cylindrical robot that is mounted on a linear gantry. The gantry 19 includes a pair of linear rails 191 that support a crossbar 192 extending between the rails 191. Only one of the linear rails 191 is shown in FIG. 2 for clarity, but the unshown rail 191 may be located nearer the top surface 12 than the rail 191 shown in FIG. 2 so that easier access may be had to the work space. In this case, the crossbar 192 may have an upwardly extending bracket (not shown) or other element to engage with the rail 191 near the top surface 12. The crossbar 192 may be driven under precise positional control along the linear rails 191, and the robot 18 is mounted to the crossbar 192 so that it may be precisely positioned along the length of the crossbar 192. The robot 18 may manipulate a tool 20, or pod, to perform various functions. For example, the tool 20A shown in FIG. 2 may be a liquid handling device that operates under the robot control. The robot 18 may interchange tools 20. For example, a tool holder 21 may support one or more alternate tools 20, such as the tool 20B, so that the robot 18 can drop one tool 20 on the tool holder 21 and pick up an alternate tool 20. The tool holder 21 may take a variety of forms, including a flat table surface on which the tools 20 may be placed or have customized tool holding features for supporting each tool 20 used by the robot 18.

In this illustrative embodiment, the alternate tool 20B may be a robotic gripping tool that enables the robot 18 to pick up, move and otherwise handle sample holders 16 or other objects in the modular station 1A. Thus, for example, the robot 18 may pick up the gripping tool 20B and use the tool 20B to grasp and remove a sample holder 16 from a hotel 15 in the storage box 17. The sample holder 16 may be withdrawn from the storage box 17 through an access 173 in the storage box 17. The access 173 may be covered by a door that is automatically opened and closed to allow access by the robot 18. The robot 18 may place the sample holder 16 in any suitable position for performing processes. For example, the sample holder 16 may be placed in a work tray 22. The work tray 22 may have a plurality of sample holder positions 22A, e.g., formed by recessed portions in the tray 22, that serve to keep the sample holders 16 in place on the work tray 22. The work tray 22 may include heating or cooling coils so that liquid samples in the storage holders 16 are maintained at a desired temperature. The temperature may be controlled for each individual position 22A or for each group of positions 22A, e.g., for each group of six positions 22A on the work tray 22. Of course, although a single work tray 22 is shown in FIG.

2, the modular station 1A may include any number of work trays 22 that each have any number of sample holder positions 22A. It should be understood, however, that such work trays 22 are optional, and even if provided, the robot 18 may perform operations on a sample holder 16 that is not located within a work tray 22.

Figure 4:
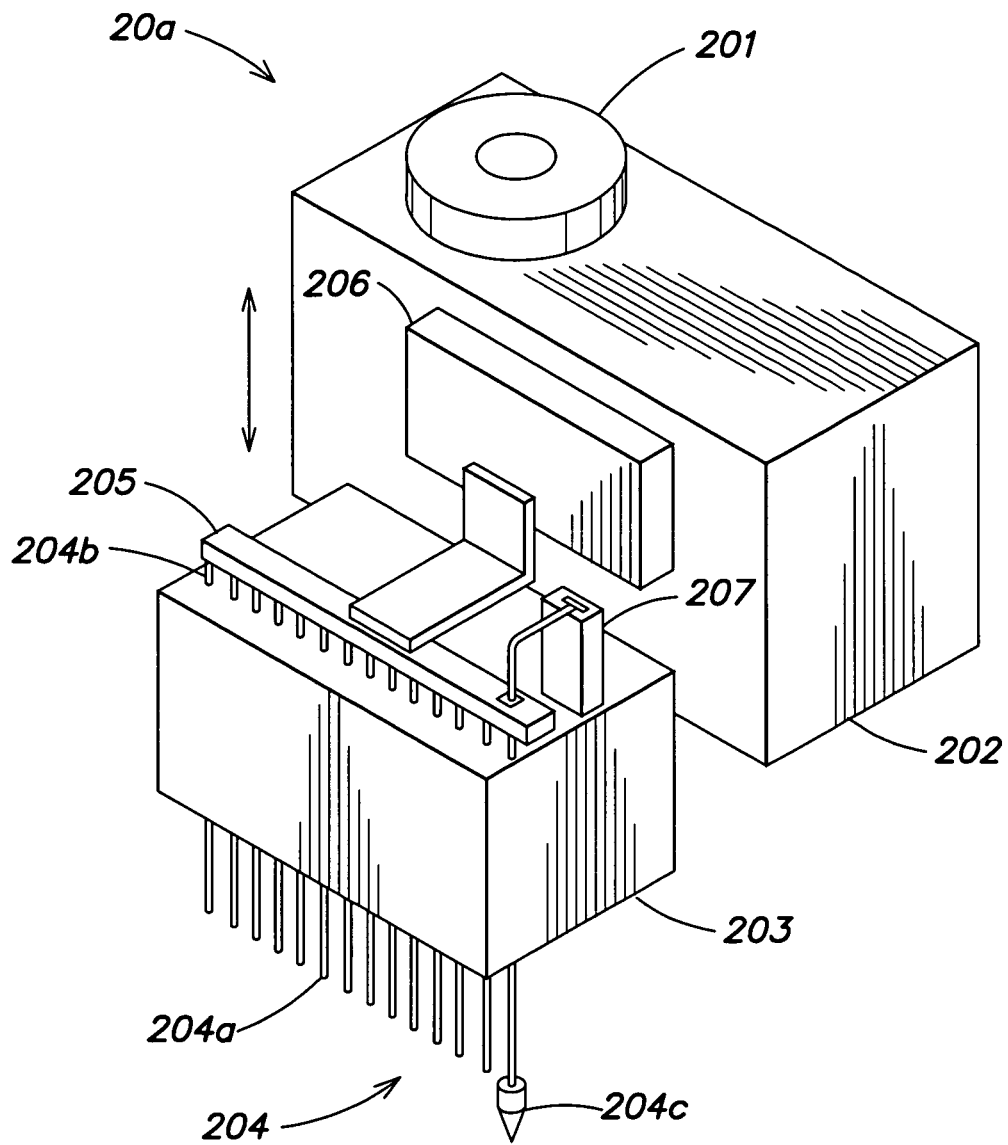
FIG. 4 is a schematic diagram of a liquid handling device in an illustrative embodiment.

When performing liquid handling operations, the robot 18 typically will pick up and use a liquid handling tool 20A to move liquid samples to and from sample holders 16 or other containers. FIG. 4 shows a schematic diagram of a liquid handling tool 20A in an illustrative embodiment. The liquid handling tool 20A includes an adapter 201 that provides a quick connect/disconnect between the robot 18 and the tool 20A and allows both mechanical and electrical connection between the robot 18 and the tool 20A. Such adapters 201 are well-known and used widely by robots having interchangeable tools. The adapter 201 is connected to a body 202 which may include a frame to support the tool 20A, electrical wiring and components, sensors, or other suitable devices. Connected to the body 202 is a pipetting block 203 which has a plurality of pipetting channels 204. Each pipetting channel 204 includes a pipette tip holder 204A that extends from a lower side of the pipette block 203. The pipette tip holders 204A each communicate with a corresponding cylinder bore (not shown) in the pipetting block 203. Each of these cylinder bores has a plunger 204B positioned within the bore and extending through a top surface of the block 203. One or more seals (not shown) within the cylinder bores create an airtight seal between the plungers 204B and the cylinder bore so that as the plungers 204B are moved upward or downward relative to the pipetting block 203, liquid may be withdrawn into or expelled from pipetting tips 204C (only one shown in FIG. 4) attached to the tip holders 204A. Upper ends of the plungers 204B are attached to a bar 205 so that when a linear servo motor 206 moves the bar 205 upward or downward along the direction shown by the double-headed arrow in FIG. 4, the plungers 204B are correspondingly moved in their respective cylinder bores and liquid material may be controllably withdrawn into and expelled from pipette tips 204C attached to the tip holders 204A.

Use of a linear servo motor 206 to control the movement of the plungers 204B provides a significant advancement over typical liquid handling devices in which the plunger 204B movement is controlled by a rotary stepper motor. Also included in this illustrative embodiment is a linear encoder 207 which also provides a significant advance over existing liquid handling systems. The linear encoder 207 provides a much more accurate indication of plunger 204B position and movement, and thus allows the linear motor 206 to more accurately control the volume of liquid material withdrawn into and expelled from each of the pipette tips 204C. Accurate volume control can be very important in some applications as the liquid sample material may be very expensive and/or the volume of liquid material expelled from a pipette tip 204C may influence the results of further processing. For example, if an insufficient volume of a liquid material is placed into a well in a microtiter plate by the liquid handling tool 20A, further processing of that liquid sample, such as amplification and separation, may not be performed properly or provide desired results.

It should be understood that the liquid handling tool 20A shown in FIG. 4 is only a schematic diagram for a liquid handling tool 20A. Thus, the particular construction and operation of the liquid handling tool 20A may vary from that shown in FIG. 4. For example, attached drawings of a 12-channel pipetter illustrate in a much more detailed way how such a liquid handling tool 20A may be constructed.

Figure 5:
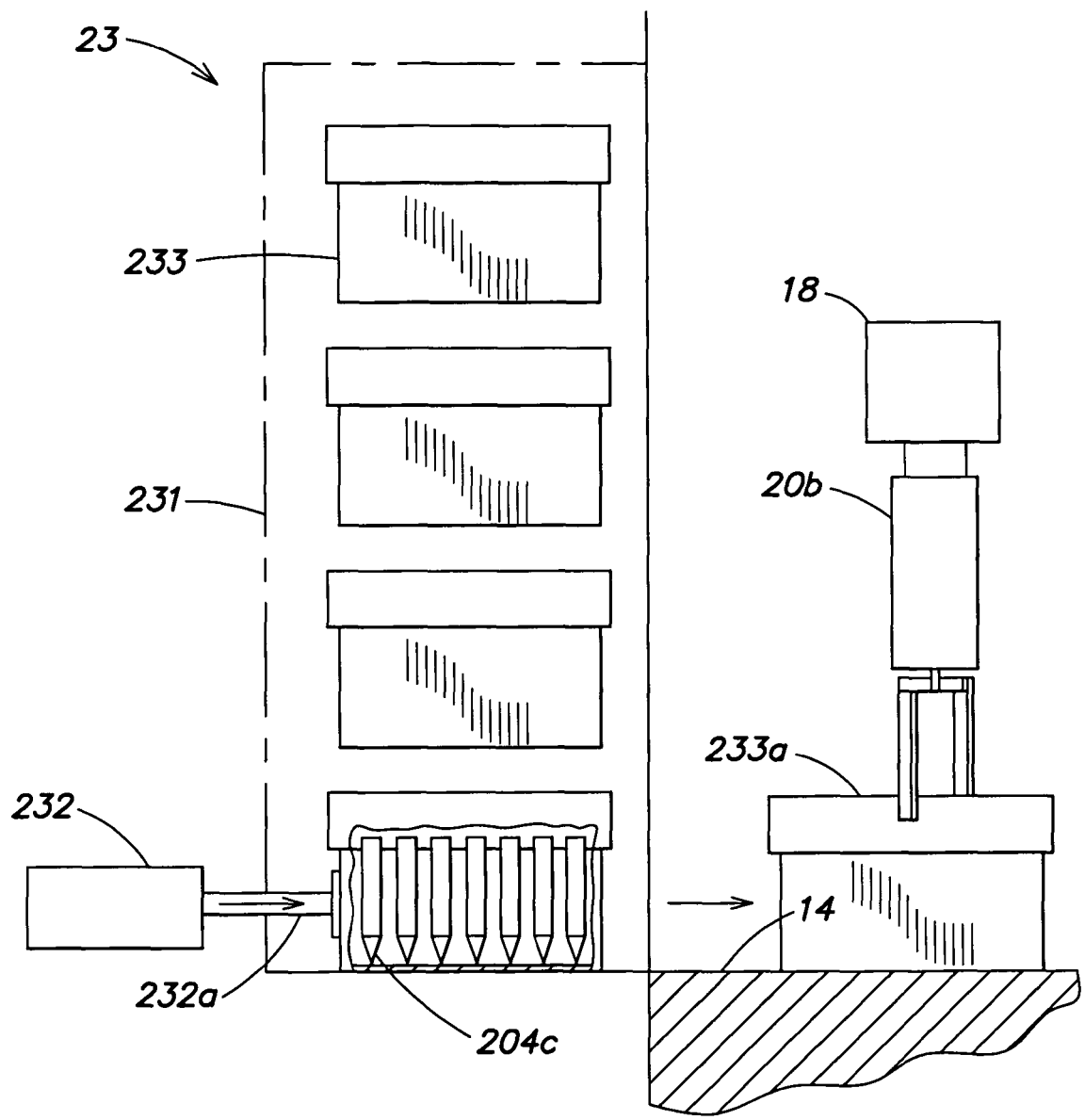
FIG. 5 is a schematic diagram of a tray feeder in an illustrative embodiment.

When performing liquid handling operations, the robot 18 may control the liquid handling tool 20A to change pipette tips 204C attached to the pipette tip holders 204A on the tool 20A. Such tip changing may be performed for various reasons, including preventing sample cross-contamination. Replacement pipette tips 204C may be supplied by a tray feeder 23 shown in FIG. 2. A more detailed view of an illustrative embodiment for a tray feeder 23 is shown in FIG. 5. In this embodiment, the tray feeder 23 includes a rack 231 that supports a vertical stack of pipette tip trays 233. Each of the pipette tip trays 233 includes a plurality of pipette tips 204C. Such pipette tip trays 233 are well-known and widely used in the art. A tip tray extractor 232 moves a bottommost tip tray 233 from left to right, as shown in FIG. 5 so that the tip tray 233 may be accessed by the robot 18. The tip tray extractor 232 may be implemented in a variety of different ways. In this illustrative embodiment, the extractor 232 includes a push rod 232A that pushes the bottommost tip tray 233 onto the work surface 14. The push rod 232A may engage with any suitable portion of the tip tray 233. In an alternate embodiment, the tip tray extractor 232 may be positioned on the work surface 14 and may pull, rather than push, the tip trays 233 onto the work surface 14. Once the tip tray 233 is suitably positioned on the work surface 14, e.g., by walls or other surfaces (not shown) that guide and hold the tip tray 233 in a known position, a gripping tool 20B on the robot 18 may remove a lid 233A from the tip tray 233, thereby exposing the pipette tips 204C in the tray 233. Of course, the robot 10 need not be used to remove the lid 233A, or the tip trays 233 may be supplied without lids 233A. With the pipette tips 204C exposed and the liquid handling tool 20A attached to the robot 18, the tip holders 204A may be aligned with tips 204C in the tray 233 and inserted into a corresponding tip 204C. The tray feeder 23, the liquid handling tool 20A or other suitable device may include the capability to determine whether pipette tips 204C are properly secured to the tip holders 204A for each of the channels 204. For example, each of the tips 204C may be moved past a photosensor that detects the presence or absence of each of the tips 204C. If one or more of the tips 204C are missing or misaligned with a tip holder 204A, new tips 204C may be placed onto the tip holders 204A. For example, the tips 204C may be removed from the tip holders 204A in any suitable way, such as by engaging the tips 204C with an ejector bar (not shown) on the liquid handling tool 20A that pushes the tips 204C off of the tip holders 204A. Other devices may be used to confirm that tips 204C are properly positioned on tip holders 204A, such as mechanical switches that change state only when a tip 204C is properly positioned on a holder 204A, video camera confirmation, and so on. Pipette tips 204C may be ejected from the tip holders 204A so that the rejected tips 204C are placed into a tip tray 233. Tip trays 233 having rejected pipette tips 204C may be removed from the work surface 14 and stacked, for example, in a way similar to that in the tray feeder 23.

With the pipette tips 204C properly positioned on the liquid handling tool 20A, the robot 18 may use the tool 20A to perform any suitable liquid handling processes, such as moving liquid materials from one sample holder 16 to other sample holders 16, other microtiter trays, etc. Sample holders 16 that are ready for processing by a next modular station, such as the amplification modular station 1B, are placed by the robot 18 (using the gripping tool 20B, for example) so that the transport device 2A can move the sample holders 16 to the modular station 1B. The transport device 2A may include at least one conveyor belt or other device suitable for moving the sample holders 16. The conveyor belt may be bi-directional so that objects may be moved in either direction between the modular stations 1A and 1B. Although devices other than conveyor belts may be used by the transport device 2A, the devices used are preferably non-robotic to spare the expense and complexity of a robot to simply move objects from one position to another. Thus, conveyor belts, slides, or other relatively simple devices are preferably used by the transport devices 2.

Using a transport device 2A, such as a conveyor belt, also allows for better isolation between modular stations 1A and 1B, since the modular stations 1A and 1B or the transport device 2A may include one or more doors that are automatically opened and closed to permit objects to move between the stations 1A and 1B. The non-robotic transport device 2A also saves the robot 18 from unnecessary movement since the robot 18 need not move sample holders 16 or other objects so that a robot within the modular station 1B can pick up the sample holder 16 or other object where the robot 18 left it. Thus, the robot 18 is left more free to perform other processes, thereby potentially increasing the number of operations that may be performed by the robot 18 in a given time period.

Using the transport devices 2 may also allow easier interconnection and/or change in relationships between modular stations 1. For example, a system 100 may originally be configured to have the arrangement shown in FIG. 1, i.e., one liquid handling modular station 1A that communicates with one amplification modular station 1B which communicates with one separation modular station 1C. However, if the liquid handling modular station 1A is able to perform its processes fast enough to provide work for two amplification modular stations 1B, a second modular station 1B may be added and the transport device 2A relatively inexpensively reconfigured to transport objects between the liquid handling modular station 1A and both of the amplification modular stations 1B. No other changes need be made to the liquid handling modular station 1A or the preexisting amplification modular station 1B regarding how objects are moved between the two. Thus, the transport devices 2 allow may allow true modularity of the system 100 components to be realized.

Once sample holders 16 are moved to the modular station 1B, a robot 18 arranged similarly to that shown in FIG. 2 and using a gripping tool 20B, may pick up the sample holder 16 and perform further processing on the liquid material in the sample holder 16. For example, the robot 18 may place sample holders 16 into a PCR thermocycling device and again remove the sample holders 16 once the thermocycling processing is complete. The modular station 1B may include a plurality of PCR thermocycling devices, e.g., up to 32 devices, so that multiple sample holders 16 may be processed at one time. For example, the modular station 1B may include sixteen PCR devices that are all serviced by a single robot 18.

As in the modular station 1A, the modular station 1B may read machine-readable codes on each of the sample holders 16 to confirm the identify of the sample holders 16 and to ensure that an appropriate process is performed on the liquid material in the sample holders 16 and/or group sample holders 16 for parallel processing. For example, after confirming the identity of a sample holder 16, the sample holder 16 may be placed in a PCR device which is then programmed (automatically by a system controller) to perform the appropriate process on the liquid material. Thus, each of the modular stations 1 may operate semi-autonomously to perform processes within the modular station 1 under the overall system-level control of a central controller, e.g., a programmed general purpose computer or other data processing apparatus. For example, the central controller may maintain a database of sample holders 16, the hotels 15 that each sample holder 16 is associated with, the identity of liquid samples associated with each sample holder 16 (each sample holder 16 may be a 96-well, 384-well or larger-number well plate that has 96, 384 or a larger number of individual liquid material samples), and the processes that are to be performed on each liquid sample in each sample holder 16. Accordingly, upon receiving a sample holder 16, each modular station 1 may confirm the identity of the sample holder 16 and receive instructions from the central controller regarding the processes to be performed on liquid material samples in the sample holders 16. The central controller may use a relational database arrangement by which each sample holder 16 or sample in a holder 16 is associated with one or more process tables in the database. The process tables may include predefined processing steps, including definitions of materials to be used in the processing of the samples. The process table association for each sample or sample holder 16 may be hierarchical, e.g., so that higher level process tables refer to lower level process tables that define standard processes. By using a relational database-driven control system, lengthy and detailed processing plans need not be generated for each sample or sample holder 16. Instead, a sample or sample holder 16 may be associated with one or more process tables which together define the processes to be performed. The central controller may also schedule the sequence of processing operations and direct the modular stations 1 to perform processes on particular sample holders 16, or samples within a sample holder 16, in a particular order. For example, the central controller may analyze the process tables associated with sample holders 16 to identify which sample holder 16 should be grouped together for parallel processing. This may be done by determining which sample holders 16 are associated with a same process table. Once parallel processing groups are determined, the central controller can instruct the modular stations to process the sample holders 16 accordingly, e.g., the modular station 1A may be instructed to place six sample holders 16 in a work tray 22, perform a same or similar set of liquid handling processes on the sample holders 16, and then move the sample holders 16 to a next processing step. The central controller can also schedule when processes are to be performed based on expected processing times for steps in an overall processing plan. Alternately, a processing plan, including parallel processing group definitions, may be provided to the central controller, e.g., by a user entering the plan at a central controller interface.

The central controller may also store a plurality of defined protocols, e.g., an association of one or more predefined process tables, that may be selected by a user, e.g., using a graphical user interface, for a set of samples to be processed by the system 100. For example, a user may specify that "Protocol 135" is to be used for a set of samples that are being input into the system 100. Thus, a user need not specifically define the particular protocol parameters each time a set of samples are provided for processing. Instead, the user may select one or more of a set of defined protocols that themselves define the processing steps, etc. for the protocol. Based on the selected protocol(s), the system controller may schedule and implement the processing to be performed, which may include reconfiguring a processing plan previously developed and currently being implemented by the system 100. (The processing plan may include a list of material samples, or sample holders 16, the processes to be performed on them by the modular stations 1, and the order in which the processes are to be performed. As processes are performed, the plan may be updated to reflect that steps have been completed, allowing a next process to be started, and so on.) Of course, the central controller may provide an interface so that a user can explicitly define the process tables, processes and/ or materials to be performed and used in a protocol, and/or allow the user to select a predefined protocol/process table and modify one or more processes or materials used in the predefined protocol/process table.

Samples that have completed the amplification processing in the amplification modular station 1B may be transported by the transport device 2A back to the liquid handling modular station 1A, if necessary for further liquid handling processes, or forwarded to the separation modular station 1C by the transport device 2B. The separation modular station 1C may be equipped with a robot 18 in a way similar to that shown in FIG. 2. Thus, the robot 18 in the modular station 1C can pick up and move sample holders 16 so that separation processing steps can be performed on the liquid material samples.

Figure 6:
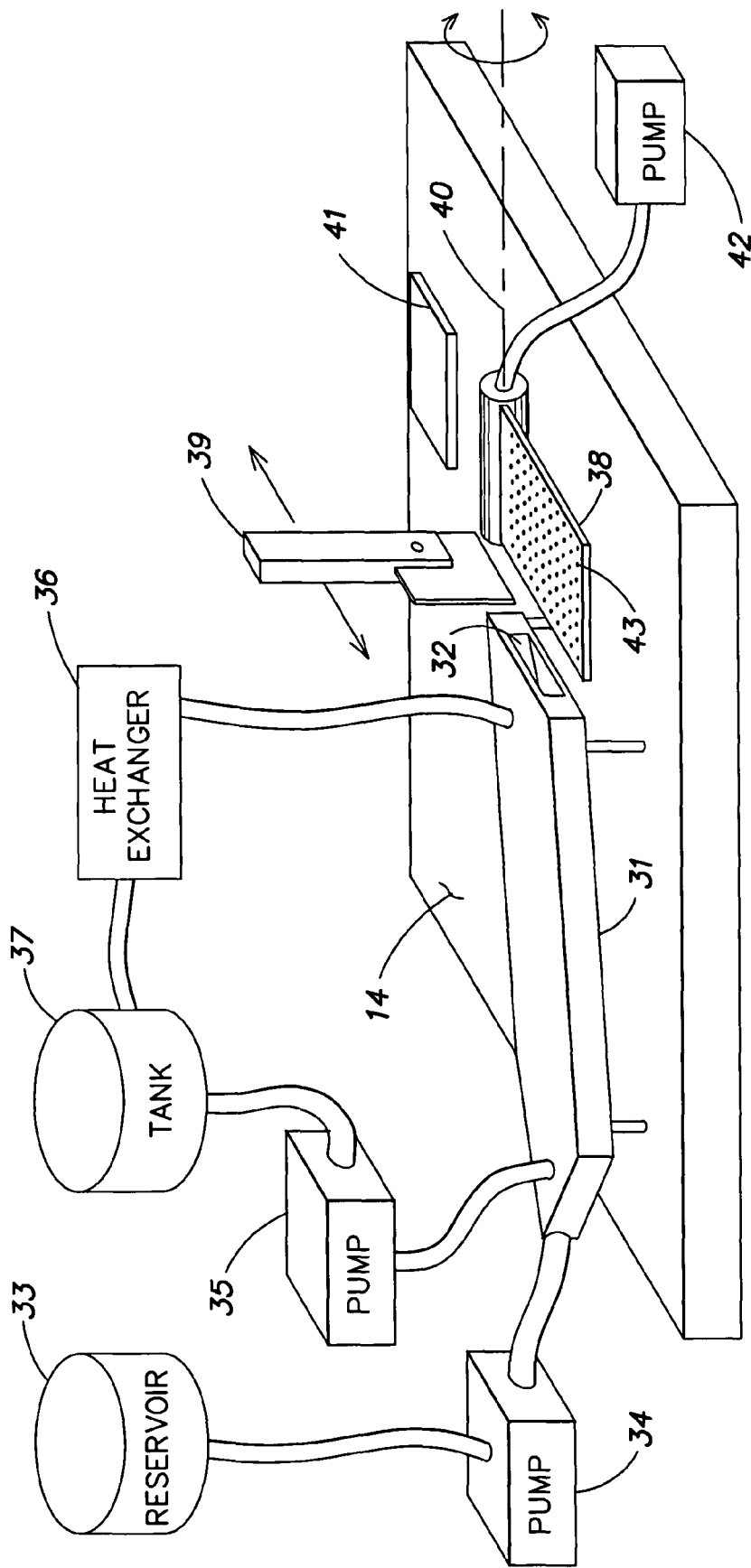
FIG. 6 is a schematic diagram of a gel extruder in an illustrative embodiment.

In this illustrative embodiment, the separation modular station 1C separates genetic fragments in the liquid material samples using gel electrophoresis. In one illustrative embodiment, the separation modular station 1C automatically creates the gels used to separate the genetic material. FIG. 6 is a schematic diagram of an automated gel extruder that may be used in the separation modular station 1C. At the center of the apparatus is the gel extruder 31 which is basically formed by a pair of parallel metal plates that are separated from each other to form an extrusion cavity 32. In one illustrative embodiment, the plates are separated approximately 0.25 inches apart and form a 10-inch wide cavity 32. Warm liquid material, e.g., including an agarose mixture, is supplied from a reservoir 33 under a pressure of approximately 16-20 psi by a pump 34 to a lower end of the extruder 31. The extruder 31 is arranged at an angle so that the warm liquid material is injected at a position that is lower than the opposite end of the cavity 32 where gels are extruded. This incline of the extruder 31 prevents, at least initially, the liquid material from exiting the extruder 31 before being cooled to form a gel. The metal plates of the extruder 31 are cooled by a chilled liquid, such as water, that is circulated by a pump 35. In this illustrative embodiment, a heat exchanger 36 is provided to cool the circulating fluid and maintain the proper temperature of the plates in the extruder 31. The heat exchanger 36 may include a chilling system, such as a heat pump or similar device. A tank 37 is also provided to store the chilled fluid, but is not necessary.

As the liquid material supplied by the pump 34 travels through the cavity 32 between the chilled metal plates, the material solidifies to form a gel at least at the point where the material exits the extruder cavity 32. In this illustrative embodiment, the pressure of the incoming liquid material forces the gel out of the extruder 31, but other mechanisms may be used to extrude the gel. The extruded gel is deposited onto a platform 38, and once the extruded gel reaches a desired size, e.g., a 10×10 inch square of gel one quarter inch thick, a knife 39 cuts the gel from the extruder 31. In this illustrative embodiment, the knife 39 is shown as having a blade that moves in a rotary motion to cut the gel, but the gel may be cut in other ways, such as by a guillotine-type blade that moves in a linear direction. Cutting of the gels may be controlled by photosensors, e.g., positioned on the platform 38, that detect that the gel has reached a suitable size. Of course, controlling how and when the gels are cut may be performed in other suitable ways.

Once the gel is cut, the platform 38 may rotate about an axis 40 as shown in FIG. 6 to deposit the gel in a tray 41 or other suitable container or surface. To prevent the gel from dislodging from the platform 38 as it rotates, a vacuum pump 42 may withdraw air from the platform 38 through holes 43 in the platform 38. Withdrawal of the air by the pump 42 provides sufficient suction to keep the gel in place until it is deposited in the tray 41. Once the platform 38 has rotated sufficiently, the pump 42 may stop withdrawing air through the holes 43 to release the gel from the platform 38 and drop it into the tray 41. Once the gel is deposited in the tray 41, the platform 38 may rotate back into position to receive another gel, and the tray 41 having a gel placed in it may be picked up and moved by a robot (not shown) and an empty tray 41 positioned in its place. It should be understood that flipping extruded and cut gels using the platform 38 or other mechanism is not required. Instead, the gels may be extruded directly onto a tray 41 or other container or surface. Also, gel cutting may be combined with flipping the gels into a tray 41. For example, an edge of the platform 38, or a cutting tool attached to the platform 38, may cut the gel as the platform 38 rotates toward the tray 41. Other suitable mechanisms for handling the extruded gels will occur to those of skill in the art.

Figure 7:
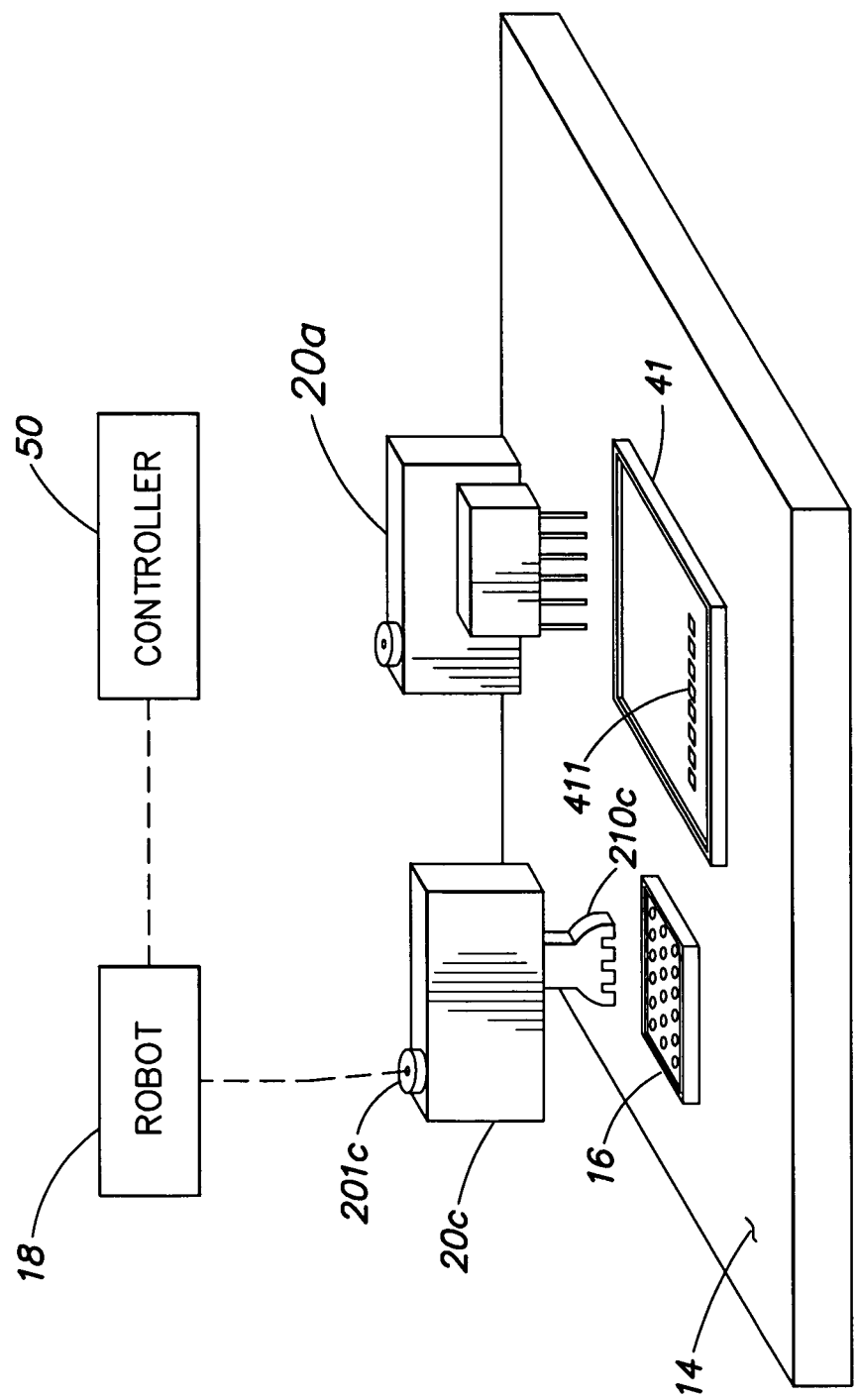
FIG. 7 is a schematic diagram of an automated material separation apparatus having a well former and liquid handling device in an illustrative embodiment.

The separation modular station 1C may use the trays 41 carrying gels to separate amplified genetic material received from the amplification modular station 1B. FIG. 7 shows a schematic diagram of another portion of the separation modular station 1C in which wells are formed in the extruded and cut gels and the genetic material is placed in the wells in preparation for applying a voltage to the gels to separate the genetic material. In this illustrative embodiment, a robot 18, which may be arranged similarly to that shown in FIG. 2, e.g., having a linear gantry and so on, uses a well forming tool 20c to form wells 411 in the gels. The well forming tool 20c includes a comb-like element 210c that is heated and pressed into the gels. In this embodiment, the comb-like element 210c has one row of four tines, and thus forms four wells at a time in a gel. It should be understood, however, that the comb-like element 210c may have any suitable number of tines and may have multiple rows of tines. In this illustrative embodiment, the comb-like element 210c is made, e.g., cut or stamped, from a metal plate and is heated by electro-resistant heating so that the tines burn or melt the wells into the gel. Current for heating the element 210c is supplied through the adapter 201c, but the element 210c may be heated in any suitable way. For example, the element 210c may normally be stored in a tool holder 21 where it is preheated and picked up by the robot 18, e.g., picked up by a gripping tool 20b that grasps the element 210c. The element 210c may be returned to the tool holder 21 for reheating and/or exchange for another tool 20 after having been used to form wells 411 in a gel.

Once wells 411 are formed in a gel, a liquid handling tool 20a may be used by the robot 18 to place liquid samples in a sample holder 16 or other holder into the wells 411. Since the robot 18 formed the wells 411 in the gel, the robot 18 can more easily register the pipette tips 204C on a liquid handling tool 20A with the wells 411 since the position of the tines on the comb-like element 210c relative to the robot 18 are known, the position of the pipetting channels 204 relative to the robot 18 are known, and the position of the robot 18 where each of the wells 411 was formed is known. From this information, the robot 18 (or its control system) can determine the appropriate robot position to load each of the wells 411 with liquid from the pipette tips 204c.

When the wells 411 are loaded with liquid material, a voltage is then applied to the loaded gels to separate the genetic material in the wells 411. Although using a voltage to separate genetic material using a gel is well known, in this embodiment, the separation modular station 1C uses the robot 18 or other tool to move the trays 41 ready for voltage application to a voltage station (not shown). The voltage station may accommodate a plurality of trays 41, such as twenty trays at any one time. Thus, twenty or more trays 41 may be subjected to a voltage separation process simultaneously. The voltage station may have a plurality of vertically oriented shelves onto which one or more trays 41 are placed. Once on a shelf in the voltage station, voltage electrodes may be inserted into the gel, e.g., by a robot or other automated device, and a suitable voltage applied.

Figure 8:
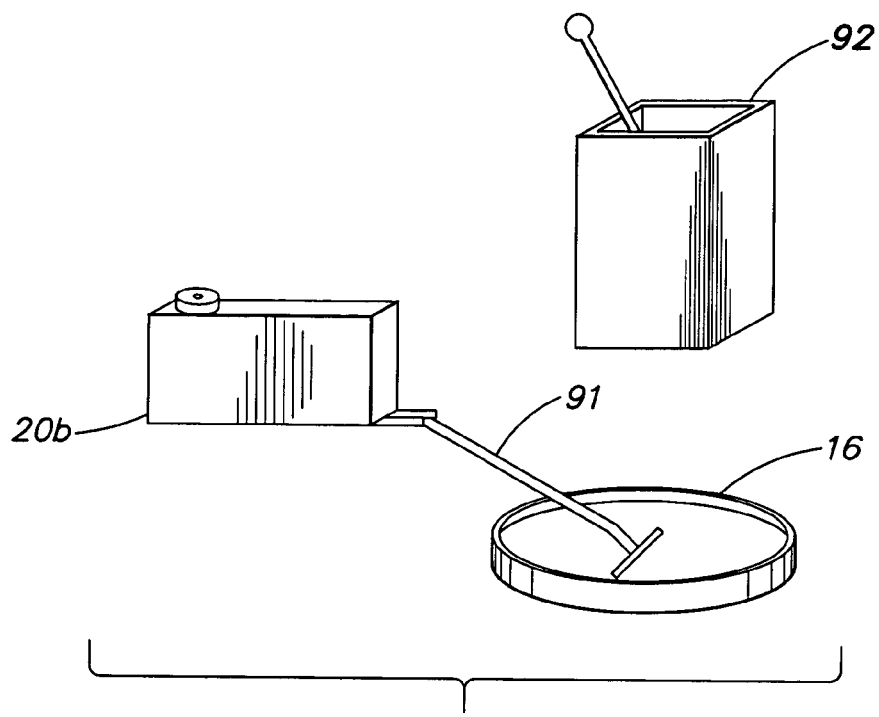
FIG. 8 is a schematic diagram of an automated material picker having vision capability in an illustrative embodiment.

Once the material in the wells 411 has been separated by the applied voltage, the trays 41 may be removed from the voltage station and selected portions of the separated material picked from the gels. For example, FIG. 8 shows a schematic diagram of an automated gel picking arrangement that may be used in the separation modular station 1C. That is, the separation modular station 1C (or other station) may have a robotically-controlled coring tool 20d that picks selected areas 412 having a desired portion of separated material. The coring tool 20d may be guided by a vision system that includes a camera 51. The vision system, which may be a software module that is part of the robot control system 50 (see FIG. 7), may use video images captured by the camera 51 to identify one or more areas 412 of the gel that have desired portions of the separated genetic material by image analysis. The vision system may also provide the location of the areas 412 to the robot control system 50 so that the robot 18 and the coring tool 20d can be controlled to pick the selected areas 412. The picked areas 412 may be used for further processing by the material processing system 100, such as extracting the genetic material from the picked areas 412 from the gel or other material, further amplification, other testing and so on. Alternately, the picked areas 412 may be output for further processing by manual processes or other automated devices.

Figure 9:
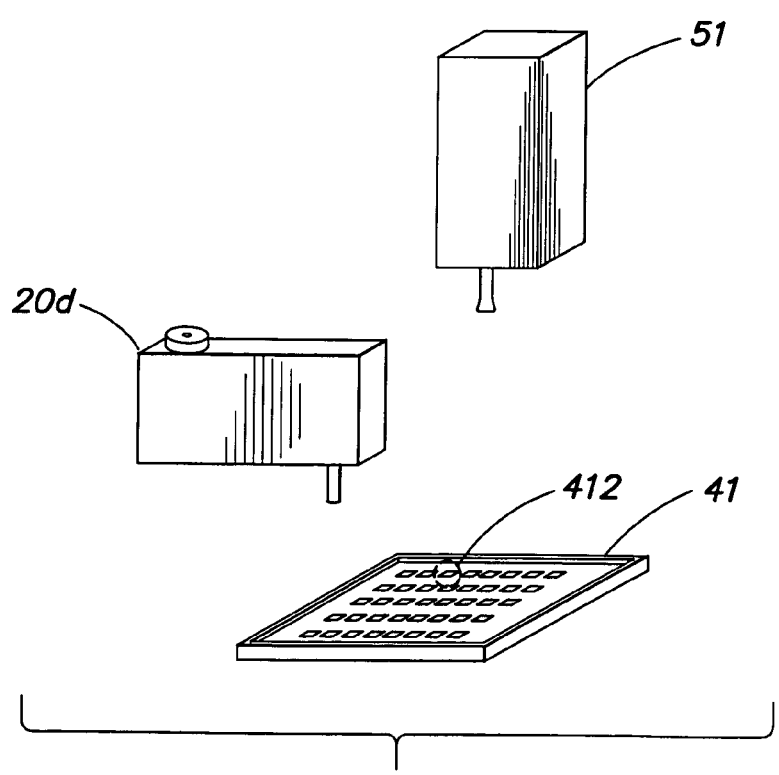
FIG. 9 is a schematic diagram of an automated plating arrangement in an illustrative embodiment.

It should be appreciated that a variety of different automated processes may be performed by the modular stations 1. For example, FIG. 9 shows a schematic diagram of a robotically-controlled gripping tool 20b performing an automated plating process. In this illustrative embodiment, the gripping tool 20b grasps and manipulates a plating wand 91 to spread a liquid material in a sample holder 16. Such plating processes are typically manually performed to spread a material, such as a liquid containing a bacterial culture, on a growth medium. Performing the plating process automatically can prevent contamination and result in a more repeatable plating process being performed on different sample holders 16. The gripping tool 20b can retrieve the plating wands 91 from a wand holder 92. In this embodiment, the wand holder 92 has a cup-like shape to hold the wands 91, but it should be understood that the wands 91 may be held and/or provided to the gripping tool 20b in any suitable way.

While the invention has been described in conjunction with specific embodiments thereof, many alternatives, modifications, and variations will be apparent to those skilled in the art. Accordingly, embodiments as set forth herein are intended to be illustrative of the various aspects of the invention, not limiting. Various changes may be made without departing from the spirit and scope of the invention.

The invention claimed is:

1. A method for forming gels suitable for use in a gel electrophoresis process, comprising:
   providing a liquid material at a first end of an enclosed extrusion cavity, the extrusion cavity having an opening at a second end opposite the first end;
   forming a solidified gel in the extrusion cavity between the first and second ends by cooling the liquid material such that the liquid material solidifies to form a, solidified gel in the enclosed extrusion cavity; and
   extruding the solidified gel from the opening at the second end of the enclosed extrusion cavity.

2. The method of claim 1, wherein the extrusion cavity is located within an extruder body; and
   the step of providing a liquid material includes providing the liquid material from a liquid material supply apparatus to a first end of the extruder body.

3. The method of claim 2, wherein the extrusion cavity is arranged so that the first end is lower than the second end.

4. The method of claim 2, wherein the extruder body includes a pair of spaced plates that define two sides of the extrusion cavity.

5. The method of claim 4, wherein at least one of the plates is cooled by a chilled liquid.

6. The method of claim 2, wherein the liquid material supply apparatus includes a pump that delivers the liquid material under pressure to the first end of the extrusion cavity.

7. The method of claim 6, wherein the pressure of the liquid material entering the first end of the extrusion cavity forces the gel to exit from the opening at the second end of the extrusion cavity.

8. The method of claim 2, further comprising using a cutting device to cut gels extruded from the second end of the extrusion cavity.

9. The method of claim 2, further comprising receiving a gel that exits from the opening at the second end of the extrusion cavity onto a rotatable platform.

10. The method of claim 9, further comprising evacuating air from the rotatable platform to create a suction force to secure gels to the platform.

11. The method of claim 1, wherein the step of forming a gel comprises cooling the liquid material between a pair of metal plates to form a gel.

12. The method of claim 1, wherein the step of providing a liquid material comprises providing the liquid material at a location at the first end of the extrusion cavity that is lower than the second end of the extrusion cavity.

13. The method of claim 1, further comprising:
   using the extruded gel in an electrophoresis process.

* * * * *

UNITED STATES PATENT AND TRADEMARK OFFICE
CERTIFICATE OF CORRECTION

| | | |
|---|---|---|
| PATENT NO. | : 8,865,474 B2 | Page 1 of 1 |
| APPLICATION NO. | : 11/429888 | |
| DATED | : October 21, 2014 | |
| INVENTOR(S) | : Michael Paschetto et al. | |

It is certified that error appears in the above-identified patent and that said Letters Patent is hereby corrected as shown below:

In the Specification:

At column 3, line 61, the word "Within" should read -- within --.

In the Claims:

In claim 1, at column 16, line 11, delete "," after the word "a".

Signed and Sealed this
Seventeenth Day of February, 2015

Michelle K. Lee
*Deputy Director of the United States Patent and Trademark Office*